United States Patent [19]
Andersson et al.

[11] Patent Number: 5,938,446
[45] Date of Patent: *Aug. 17, 1999

[54] METHOD AND DEVICE FOR A PRODUCT INTENDED TO BE INTRODUCED INTO THE HUMAN BODY, AND SCANNING DEVICE FOR A MODEL OF THE PRODUCT

[75] Inventors: Matts Andersson, Lerum; Magnus Persson, Vanersburg, both of Sweden

[73] Assignee: Nobel Biocare AB, Goteborg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/652,504

[22] PCT Filed: Oct. 3, 1995

[86] PCT No.: PCT/SE95/01131

§ 371 Date: Aug. 6, 1996

§ 102(e) Date: Aug. 6, 1996

[87] PCT Pub. No.: WO96/10371

PCT Pub. Date: Apr. 11, 1996

[30] Foreign Application Priority Data

Oct. 4, 1994 [SE] Sweden ................................. 9403345

[51] Int. Cl.⁶ .................................................. A61C 13/00
[52] U.S. Cl. ...................................... 433/223; 364/474.03
[58] Field of Search ..................................... 433/213, 223, 433/229; 364/474.03, 474.05, 474.37

[56] References Cited

U.S. PATENT DOCUMENTS

| | | | |
|---|---|---|---|
| 5,440,496 | 8/1995 | Andersson et al. | 364/474.05 |
| 5,497,336 | 3/1996 | Andersson et al. | 364/474.03 |
| 5,587,912 | 12/1996 | Andersson et al. | 364/468.04 |
| 5,607,305 | 3/1997 | Andersson et al. | 433/223 |
| 5,652,709 | 7/1997 | Andersson et al. | 364/474.03 |

FOREIGN PATENT DOCUMENTS 0 541 500  10/1992  European Pat. Off. .

*Primary Examiner*—Ralph A. Lewis
*Attorney, Agent, or Firm*—Pollock, Vande Sande & Amernick

[57] ABSTRACT

A method and apparatus for manufacturing a product for use in the human body using a model having different parts are provided. The method comprises the steps of determining the position of the parts with an apparatus which generates first information related to the position of the parts. The contours of the parts are then scanned with a scanning members, which is functionally separate from the apparatus, and which represents the contour with electrical signals. The electrical signals are supplied to a computer unit which transforms the electrical signals into second information which is arranged in files. The first information and second information is processed concurrently with a computer program run on the computer unit, whereby the positions of the parts in a construction are represented on a computer screen. The processing information representing a construction is then provided from the computer unit to manufacturing equipment which is used to make the product.

10 Claims, 2 Drawing Sheets

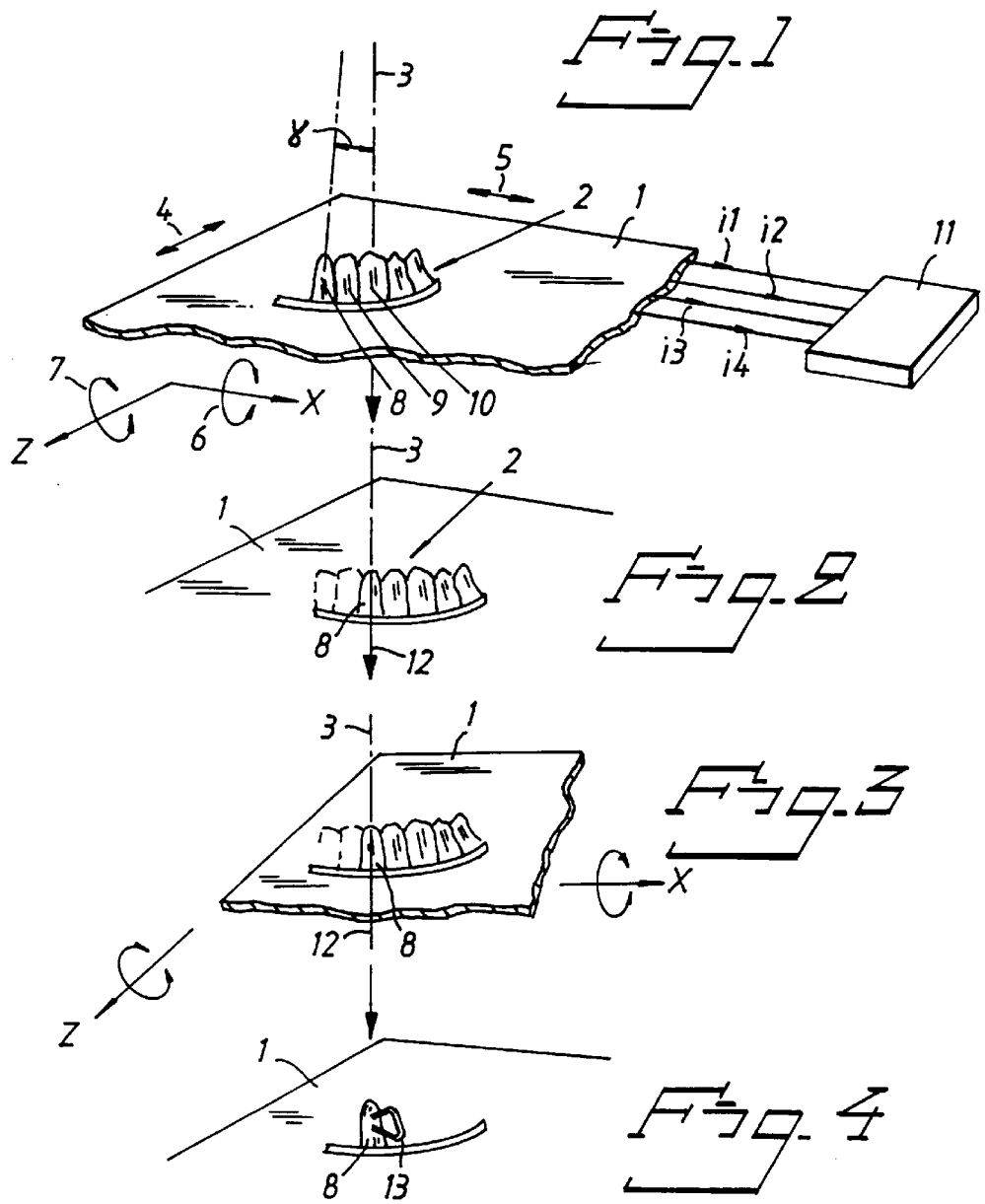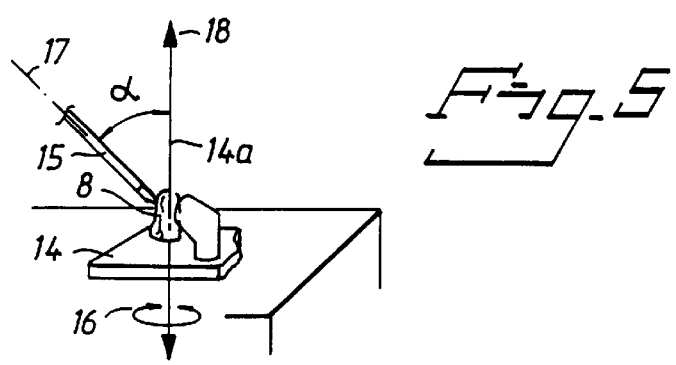

METHOD AND DEVICE FOR A PRODUCT INTENDED TO BE INTRODUCED INTO THE HUMAN BODY, AND SCANNING DEVICE FOR A MODEL OF THE PRODUCT

FIELD OF THE INVENTION

The present invention relates to a method for manufacturing a product which can be used in the human body, preferably a dental bridge, with the aid of a model comprising different parts, for example preparations. The method uses a scanning unit by means of which the contours of the parts read off and represented by electrical, preferably digital, representations. Also included is a computer unit (micro-processor) which operates with data or information items which can be related to the representations and which are arranged in files. With the aid of a computer program, for example of the example, of a CAD program, the computer processes the data in cooperation with an operator in order to create, on a computer screen, a construction based on the read-off representations. The computer can also provide processing information items representing the construction and which are used in equipment for manufacturing or machining of the construction, which can, in this case be made in the form of a blank, for example of titanium.

The invention also relates to a device for implementing method. The invention furthermore deals with a device for scanning parts of a model, preferably a model in the form of a dental bridge or equivalent dental product with parts in the form of one or more preparations, for manufacture of a construction. A digital representation, obtained as a result of the scanning or reading, of the contours of the parts or preparations is obtained from the scanning unit and supplied to the computer. Also included in the representation are data concerning the mutual positions of the parts or the preparations on the model in question. The computer unit creates on the screen, as a function of the supplied representation and with the aid of a program, for example a CAD program, and in cooperation with a user or operator, a construction, for example a dental bridge, which is based on the model.

BACKGROUND OF THE INVENTION

In the manufacture of dental bridges, for it is already known to use a scanning unit and computer for simulating a construction based on the scanning. The computer can also, in a known manner case, calculate machining coordinates for production of the construction in question.

However, there is a need to be able to produce dental bridges, for instance, in a relatively technically simple and computerized manner. Thus, it is important to indicate correctly not only the different shapes of the dental bridges, but also the relationship between the parts, at the same time as using an appropriate and rapid scanning function. The present invention solves this problem, among others.

In the manufacture of dental products, it has been advantageous to use for scanning a scanning unit in which the reading function (the beam, needle, etc) is directed obliquely to the axis of the respective dental bridge part, and to rotate the dental bridge part and its axis during the scanning. In this way, it is possible to operate in the polar coordinates system, which reduces reading times, data quantities, etc., and despite which, allows complicated contours to be read off. However, there is a clear problem in combining such a tracer principle with computer-aided construction in accordance with the above. The invention solves this problem too.

It is important that known equipment, such as scanning apparatuses, computers, computer programs, etc., could be used. Thus, for example, it is advantageous if standard software can be used. The invention also solves this problem and permits the use of known of CAD programs for producing the construction.

SUMMARY OF THE INVENTION

The feature characterizing a method according to the present invention is that the position of the respective preparation in the construction is determined using an apparatus or levelling apparatus which operates separately from the scanning unit, at least from the functional point of view. The apparatus generates information items which can be related to the positions of the preparations and which are run concurrently with or transform the read-off representations (the files) in the computer. In this the mutual positions of the preparations in the construction which is being made are indicated on the computer screen and are then used for manufacturing the dental bridge.

In a preferred embodiment, use is made of a support plane or a levelling platform on which the model arranged and can be displaced in the plane so that the preparations can be moved or adjusted to a vertical position. The platform or plane can be turned about two axes, which extend through the plane and are at right angles to one another. This provides, in each reading position, a vertical position for the preparation in the model such that the scanning unit, which traces the contour of the respective preparation, can read off the whole contour, without any undercuts or areas being concealed from the scanning unit. The adjustments of the model in relation to the plane, i.e. the position of the model in the X and Z directions and the inclination of the plane or platform in the respective reading position, are detected and indicated by equipment. The detected information items are thereafter transferred to the computer unit which uses the information in question for concurrent running in the computer. The information from the equipment is also arranged in files which can be run concurrently in the computer equipment.

Further embodiments of the novel method are evident from the attached subclaims relating to the method.

A device for scanning a model according to the present invention can be regarded as being characterized in that a support member, for example a levelling platform, is arranged to support the model, which can be activated on a [lacuna] relative plane, i.e. either the model is displaced relative to the plane or the plane is displaced with the model fixed, so that the preparations can assume one or more reading positions. The support plane or the levelling platform is arranged such that it can be turned or tilted so that the respective preparation is moved to a desired position in the vertical direction. By means of this adjustability in the vertical direction, the contour of the respective preparation can be made accessible to the scanning unit used in conjunction with the invention. The position of the model in the X, Z plane, and the inclinations of the plane or the platform in the respective reading positions, are read off by means of equipment which generates information for the computer concerning the adjustments of the model and plane/platform. The information can, upon execution or processing in the computer, and upon the interaction with an operator, represent the positions of the preparations in the construction formed on the computer screen. In one embodiment, the formed construction is sectioned upon production of machining coordinates.

By means of the above described method and device reading equipment which is presently known can be used for inputting basic data for construction of bridges into a computer. By means of the invention, it is possible for data describing the positions of the individual preparations relative to one another to be collected by the scanning function.

BRIEF DESCRIPTION OF THE FIGURES

A method and device according to the invention will be described hereinbelow, at the same time with reference to the attached drawings in which:

FIGS. 1–7 show successive manufacturing stages for production of a construction unit based on a model.

DETAILED DESCRIPTION OF THE INVENTION

Figure 6:
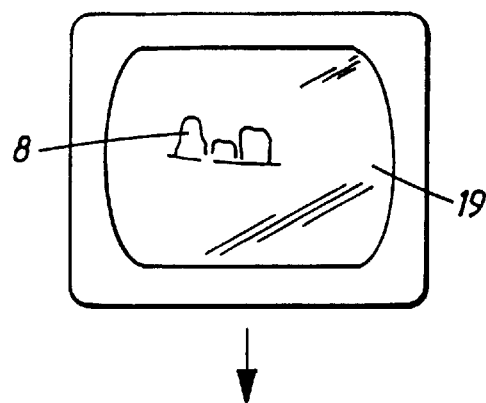

In FIG. 1, reference number 1 indicates a plane which can consist of a support platform of a levelling apparatus. A model 2 is applied on the platform. The plane or the platform has an axis 3 which extends at right angles to the plane 1. The axis 3 represents a reading position. The model is displaceably arranged on the platform in the directions of the arrows 4, 5. The platform operates with two axes which are at right angles to one another and which are here designated as the X and Z axes. The plane or the platform 1 can be turned about the said axes in the directions of the arrows 6 and 7. The model 2 includes a number of preparations 8, 9, 10, etc. The model can alternatively be fixed in the platform 1 in a known manner, in which case the platform, in turn, can be displaceable in the directions of the arrows 4 and 5. In this way, each preparation can be brought one at a time into line with the reading position, represented by the line 3. Equipment 11 is, in this case, arranged to trace the X and Z positions as well as the current angles of rotation of the axes 6 and 7. The tracing can be effected in a known manner.

In FIG. 2, the model 2 has been displaced with the aid of the platform 1 so that the axis 12 of the preparation 8 coincides with the axis 3 which represents the tracer position. This movement of the platform is indicated by tracer signals i1 and i2 in FIG. 1, which tracer signals are input to the tracer equipment 11.

The next step is to orient the preparation 8 in the vertical direction. According to FIG. 1, the preparation is inclined in relation to the axis 3 by an angle gamma. This inclination means that undercuts and certain areas are inaccessible for the scanning which is effected in the subsequent operational step. There is therefore a need to carry out the straightening of the preparation 8. In accordance with FIG. 3, this is done by the plane 1 being turned about the axes X and Z. In this way, the axis 12 of the preparation 8 can be made to coincide fully with the axis 3 or to coincide essentially with this axis. These changes in the angle of rotation of the axes are represented in FIG. 1 by signals i3 and i4. These signals are recorded in the tracer equipment 11.

In accordance with FIG. 4, the preparation 8 can be provided with a handle 13 or other gripping member, with which the preparation can be transferred to a scanning unit according to FIG. 5. The scanning unit also has a rotating platform 14 on which the preparation 8 can be applied or fixed in a defined position. The scanning apparatus is of the type which has a tracer function 15 in the form of a needle, optical tracer, etc. A rotation arrow for the said platform 14 is indicated by 16. The longitudinal axis of the tracer member or tracer function is indicated by 17. The tracer apparatus is characterized by the fact that the platform 14 is rotated, at the same time as the tracer member 15 and the preparation 8 move reciprocally in the vertical direction 18. Either the platform can be stationary in the vertical direction and the tracer function can move in the vertical direction, or vice versa. Alternatively, both the platform and the tracer function can be vertically displaceable. The handle can be removed during this tracing operation. The attachment of the handle 13 can also be made on a part of the preparation which will not be traced by the scanning equipment, which means that the handle is not in the way during scanning.

Figure 7:
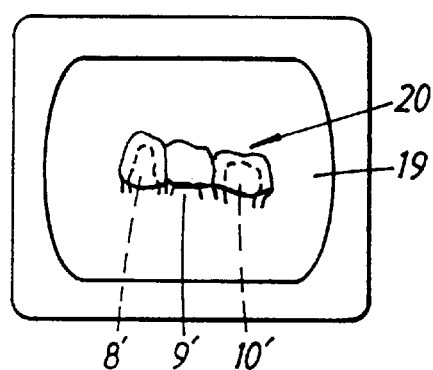

FIG. 6 shows a computer screen 19 of a computer of a known type. The preparations forming part of the bridge or equivalent are transformed on the basis of the read-off off data which is input to a CAD program. On the preparations, a bridge will be constructed in accordance with FIG. 7. The construction procedure takes place in a known manner by interaction between the computer and a user or operator. In FIG. 7, a bridge produced on the preparations 8', 9' and 10' is indicated by 20. The bridge is constructed and sectioned in the computer. The parts are then transformed back so that milling takes place about the axis of rotation 14a which is used during the reading-off.

Figure 8:
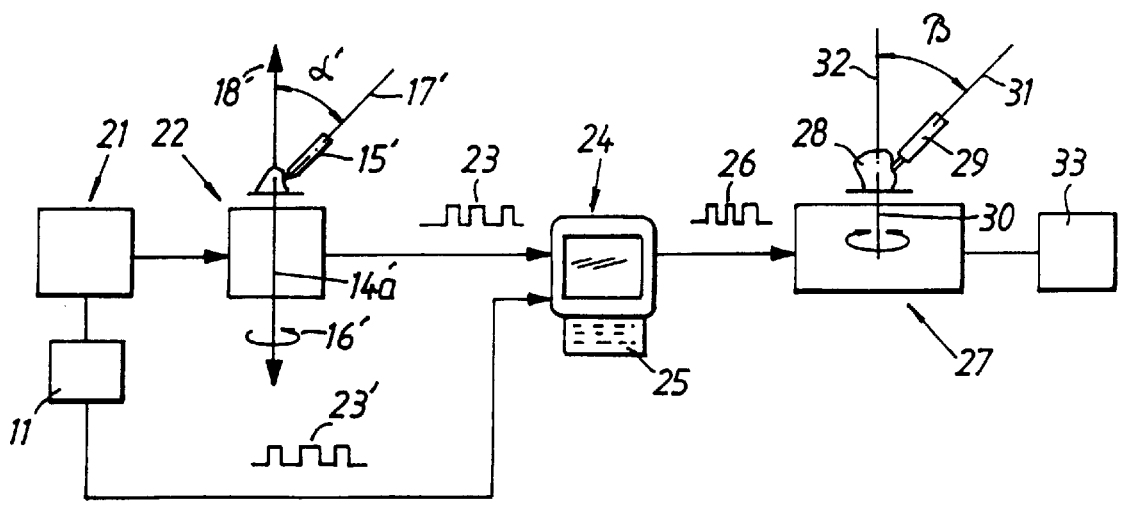
FIG. 8 shows, in circuit diagram form, processing stations included in processing equipment according to the invention.

FIG. 8 shows the entire chain of production. The levelling function described above is carried out at a first station. The said scanning function takes place at a second station 22. The axis of rotation is indicated by 14a'. The reference labels in other respects correspond to those which are used in FIG. 5, but with a prime symbol added. The digital representation which is obtained from the scanning function is shown by 23 in FIG. 8. The computer used in this connection is arranged at a station 24 and functions in accordance with the above. The computer is provided with a terminal 25 for interaction with a user. Machining or milling information is indicated by 26, and machining equipment by 27. The machining from a blank 28 also takes place in the polar coordinates system. A tool 29 is indicated in principle and symbolizes a milling cutter or other tool. The blank is rotated about a vertical axis 30. The axis 31 of the tool is inclined, in relation to the axis 32 of the blank, by an angle beta. In a preferred embodiment, the angle beta is the same size as the angles alpha and alpha'. The levelling equipment has the effect that the computer can be fed information which relates to the signals i1, i2, i3 and i4 and which information constitutes digital information 23'. The last-mentioned information is also arranged in files associated with the computer. The data in the files for the information 23, 23' is run concurrently and is used by the computer for producing the construction on the computer screen.

Since the reading-off function can read off only one preparation at a time, the data describing the mutual relationship between the preparations must therefore be collected in another apparatus in accordance with the above. This is called a levelling apparatus according to the above, since the rows of teeth can be straightened both in regards to angle and translation.

Collection of the data which is required can be carried out in the following way:

1. The preparation in question is translated in the X and Z directions so that it is placed in the "read-off position" on the levelling platform.

2. The preparation is straightened by means of the platform being rotated about the X and Z axes so that it can be read off without any undercuts or the like arising.

3. The position of the preparation in the X and Z directions, and also the angles about the X and Z axes, are read off.

4. A "handle" is secured on the preparation. With the aid of the "handle", the preparation can be transferred easily to the reading-off function. The preparation is then read off in a known manner.

The data which has been read off in the levelling apparatus is now used for transforming the read-off files so that they can be seen in their correct positions in a CAD program. The bridge is then be constructed in the CAD program using the input preparations as a basis.

The bridge constructed in the CAD program is sectioned in the computer and is transformed back so that the production basis for the inner shapes of the included parts is milled about the center of rotation with which they were read off. That is to say, the read-off file functions as production basis in the same way as for single crowns. This is to ensure that the transformation will not have an adverse effect on the accuracy. The accuracy requirements are lower for the outer shapes, which are thus those which are transformed.

The bridge parts are thereafter joined together in the usual way, by laser welding 33 in a known manner.

The invention is not limited to the embodiment which is shown hereinabove by way of example, but instead can be the subject to modifications falling within the scope of the attached patent claims and the inventive concept.

We claim:

1. A method for manufacturing a product for use in the human body with a model having different parts, said method comprising the steps of:
   determining the relative positions of the different parts in the model with an apparatus which generates first information related to the positions of the parts;
   scanning the contours of the parts with a scanning means, which represents the contour with electrical signals;
   supplying the electrical signals to a computer unit;
   transforming said electrical representation into second information arranged in files;
   processing said first information and second information concurrently with a computer program run on said computer unit, whereby positions of the parts in a construction are represented on a computer screen; and
   providing processing information representing the construction from said computer unit to manufacturing equipment.

2. The method of claim 1 further comprising the steps of:
   supporting the model on a platform in the apparatus;
   moving the parts one at a time to at least one reading position;
   rotating the platform, in each reading position, about at least two axes to provide a vertical position of each part in relation to the scanning unit, whereby the scanning unit scans the whole contour of the part;
   supplying information about the position of the model on the platform and the angles of rotation about the axes to the computer unit; and
   processing said information together with said second information to determine the mutual positions of said parts in said construction.

3. The method of claim 1 further comprising the steps of:
   providing a handle on the part;
   moving the part via the handle from the apparatus to the scanning means.

4. The method of claim 1 further comprising the steps of:
   sectioning the construction, produced by the computer program, in the computer unit; and
   providing information on the structure and position of the sections to the machining equipment.

5. The method of claim 4 further comprising the step of joining the sections together my means of laser welding.

6. The method of claim 1 wherein said electrical signals serve as a production basis for inner shapes of the parts.

7. A method for manufacturing a product for use in the human body with a model having different parts, said method comprising the steps of:
   determining the position of the parts with an apparatus which generates first information related to the positions of the parts;
   scanning the contours of the parts with a scanning means, which represents the contour with electrical signals;
   supplying the electrical signals to a computer unit;
   transforming said electrical representation into second information arranged in files;
   processing said first information and second information concurrently with a computer program run on said computer unit, whereby positions of the parts in a construction are represented on a computer screen; and
   providing processing information representing the construction from said computer unit to manufacturing equipment, and
   wherein said determining the positions and generating said first information includes:
     supporting the model on a platform in the apparatus;
     moving the parts one at a time to at least one reading position;
     supplying information about the position of the model on the platform and the angles of rotation about the axes to the computer unit; and
     processing said information together with said second information to determine the mutual positions of said parts in said construction.

8. Apparatus for use in manufacturing a product for use in the human body with a model having different parts, said apparatus comprising:
   scanning means for reading off contours of a part and representing said contours with electrical representations;
   a levelling platform moveable and tiltable about at least two axes which extend through said platform, whereby each said part of said model is aligned with one or more reading position axes with respect to said scanning means;
   means for receiving and translating information about the position of said part and said levelling platform to a computer unit;
   a computer unit communicating with said scanning means and said means for translating and receiving information about the position of said part and said platform, and said electrical representations, whereby said computer unit determines processing information, representing the correct mutual positions of said parts in a construction; and
   means for communicating said processing information to manufacturing equipment.

9. The apparatus of claim 8 wherein said levelling platform is displaceable in the x-z plane.

10. Apparatus for manufacturing a product for use in the human body with a model having different parts, said apparatus comprising:

means for moving said parts one at a time to at least one read off position, wherein an axis of each said part is aligned with one or more reading axes and wherein said means is moveable about at least two axes extending through a plane;

scanning means for reading a contour of said part;

means for supplying a digital representation of a function of said contour and read off position and angles of rotation to a computing means for creating on a screen a representation of a construction based on said model as a function of said digital representation indicating correct positions of said parts in said construction.

* * * * *

UNITED STATES PATENT AND TRADEMARK OFFICE
CERTIFICATE OF CORRECTION

PATENT NO. :  5,938,446
DATED       :  August 17, 1999
INVENTOR(S) :  Andersson et al.

It is certified that error appears in the above-identified patent and that said Letters Patent is hereby corrected as shown below:

The second inventor's city of residence is --Vanersborg--, not "Vanersburg"

Signed and Sealed this

Eleventh Day of January, 2000

Attest:

Q. TODD DICKINSON

Attesting Officer      Acting Commissioner of Patents and Trademarks